(12) United States Patent
Luke et al.

(10) Patent No.: US 11,154,529 B2
(45) Date of Patent: *Oct. 26, 2021

(54) PHOSPHAPLATIN LIQUID FORMULATIONS

(71) Applicant: Phosplatin Therapeutics Inc., New York, NY (US)

(72) Inventors: Wayne D. Luke, West Lafayette, IN (US); Tyler D. Ames, Long Island City, NY (US)

(73) Assignee: Phosplatin Therapeutics Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/091,873

(22) PCT Filed: Apr. 5, 2017

(86) PCT No.: PCT/US2017/026139
§ 371 (c)(1),
(2) Date: Oct. 5, 2018

(87) PCT Pub. No.: WO2017/176880
PCT Pub. Date: Oct. 12, 2017

(65) Prior Publication Data
US 2020/0323810 A1  Oct. 15, 2020

Related U.S. Application Data

(60) Provisional application No. 62/319,047, filed on Apr. 6, 2016.

(51) Int. Cl.
*A61K 31/282* (2006.01)

(52) U.S. Cl.
CPC ................. *A61K 31/282* (2013.01)

(58) Field of Classification Search
CPC .................................................. A61K 31/282
See application file for complete search history.

(56) References Cited

U.S. PATENT DOCUMENTS

2013/0165680 A1  6/2013  Bose et al.
2014/0288321 A1  9/2014  Luke et al.

FOREIGN PATENT DOCUMENTS

| CN | 104010508 A | | 8/2014 |
|----|----|----|----|
| GA | 2818933 A1 | | 7/2012 |
| WO | WO 2005/000858 | * | 6/2005 |
| WO | 2011153365 A1 | | 12/2011 |
| WO | 2012096722 A1 | | 7/2012 |
| WO | 2013052839 A1 | | 4/2013 |
| WO | 2013176764 A1 | | 11/2013 |

OTHER PUBLICATIONS

Moghaddas et al., "Phophaplatins, next generation platinum anti-tumor agents: A paradigm shift in designing and defining molecular targets," Inorganica Chimica Acta (2012); 393:173-181.
Corte-Rodriguez et al., "Quantitative evaluation of cellular uptake, DNA incorporation and adduct formation in cisplatin sensitive and resistant cell lines: Comparison of different Pt-containing drugs," Biochemical Pharmacology (2015);98:69-77.

* cited by examiner

*Primary Examiner* — Shirley V Gembeh
(74) *Attorney, Agent, or Firm* — Fox Rothschild LLP

(57) ABSTRACT

Pharmaceutical compositions of phosphaplatin compounds, in particular buffered stable liquid formulations of pyro-dach-2 ready for use in the treatment of various cancers, and methods of preparation are disclosed.

20 Claims, 2 Drawing Sheets

PHOSPHAPLATIN LIQUID FORMULATIONS

CROSS-REFERENCE TO RELATED APPLICATIONS

This application is the U.S. National Phase of International Patent Application No. PCT/US2017/026139, filed Apr. 5, 2017, which claims the benefit under 35 U.S.C. § 119(e) of U.S. Provisional Application No. 62/319,047, filed on Apr. 6, 2016, both of which are incorporated herein by reference in their entirety.

FIELD OF THE INVENTION

The present invention relates to pharmaceutical compositions of phosphaplatin compounds useful as anticancer agents, in particular stable liquid formulations ready for use in the treatment of various cancers.

BACKGROUND OF THE INVENTION

Monomeric phosphaplatin complexes have demonstrated great potential for treatment of a variety of diseases, including a broad range of cancers. See, e.g., WO 2009/021082, WO 2011/153365, and WO 2012/096722. Like many therapeutically useful platinum compounds, phosphaplatin complexes are usually administered parenterally, e.g., intravenous ("i.v." or "iv") injections. Drugs for parenteral administration are typically formulated as liquids, or as lyophilized solids which require reconstitution with a sterile vehicle prior to administration. Liquid formulations are highly preferable to lyophilized formulations because a) they are more economical and simpler to manufacture, and b) they are much easier to administer as they do not require reconstitution with a sterile vehicle prior to use. The pH of liquid drug formulations for iv administration are typically formulated at a pH range near the physiological range of blood pH (7.3-7.4) to avoid the clinical challenges associated with administration of a drug formulation whose pH differs significantly from that of blood. Liquid formulations that are stable and easily stored at the ambient temperature are highly preferable to liquid or lyophilized formulations, which must be stored at refrigerated or frozen conditions. Due to the possible degradation of monomeric phosphaplatin complexes in aqueous solutions, especially under acidic conditions, preparation of stable ready-to-use liquid formulations of these compounds remains a challenge.

SUMMARY OF THE INVENTION

The present invention, in one aspect, provides liquid pharmaceutical compositions comprising a phosphaplatin compound and an aqueous buffer solution having pH at or above 7, with a preferred pH range of 7-9. The buffer solution is an aqueous solution comprising a phosphate salt, a carbonate/bicarbonate salt, or a combination thereof.

In some embodiments, the phosphaplatin compound is a pyrophosphato-platinum (II) complex having a formula of (I) or (II):

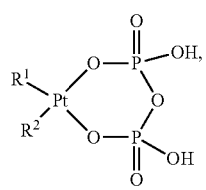

(I)

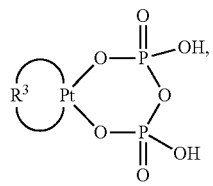

(II)

or a salt thereof, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic or aromatic 1,2-diamines.

In some more preferred embodiments, the phosphaplatin compound is selected from the group consisting of trans-1,2-cyclohexanediamine-(dihydrogen pyrophosphato)platinum(II) ("trans-pyrodach-2"), either of the two enantiomers (R,R)-pyrodach-2 and (S,S)-pyrodach-2, and cis-1,2-cyclohexanediamine-(dihydrogen pyrophosphato)platinum(II) ("cis-pyrodach-2").

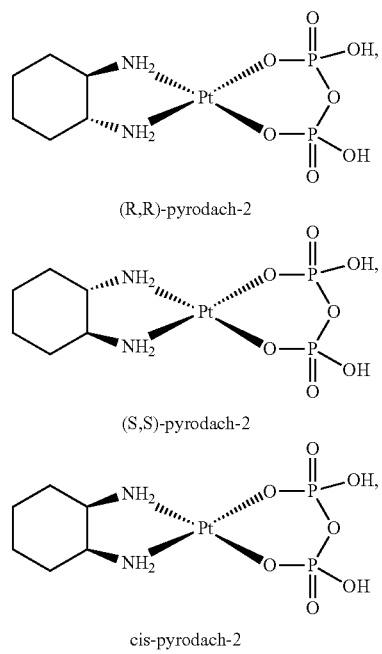

(R,R)-pyrodach-2

(S,S)-pyrodach-2 cis-pyrodach-2

The most preferred embodiments of the formulations demonstrate the potential for multi-year stability at the ambient temperature. The formulations afford a sterile concentrated solution of (R,R)-pyrodach-2 that is easily diluted in standard i.v. fluids used in i.v. administration of cancer drugs or a sterile solution at a suitable concentration in a vial ready for use on a patient.

In another aspect, the present invention provides processes for making liquid formulations, in particular ready-to-use formulations, of phosphaplatin compounds in a buffer solution as described here, the process comprising the steps of: a) dissolving a phosphaplatin compound in an aqueous buffer comprising a sufficient amount of hydroxide base such that the pH remains at or above 7; b) optionally adding a hydroxide base to adjust the pH to a desired range, and c) filtering the solution to obtain a liquid formulation.

In another aspect, the present invention is directed to use of a stable liquid formulation according to any embodiment disclosed herein in the treatment of a cancer.

These and other aspects of the present invention will be better appreciated by reference to the following drawing, detailed description and claims.

DETAILED DESCRIPTION OF THE INVENTION

Figure 1:
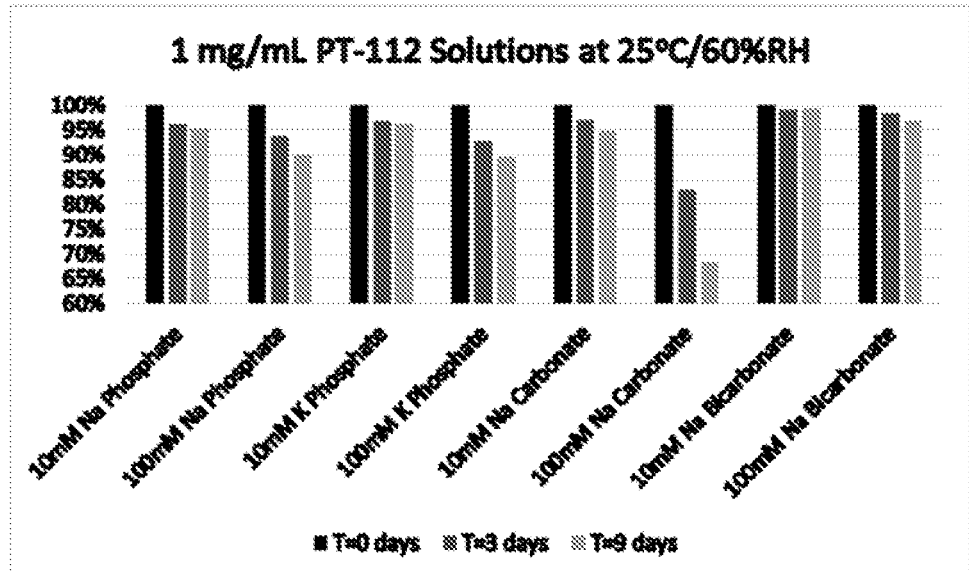
FIG. 1 illustrates the potency of capped 1 mg/mL (R,R)-pyrodach-2 solutions in various buffers stored in stability chambers controlled at 25° C./60% RH, as monitored by HPLC.

In one aspect, the present invention provides a pharmaceutical composition comprising a phosphaplatin compound and an aqueous buffer solution having pH at or above 7.

In one embodiment of this aspect, sometimes preferred, the pharmaceutical composition is a ready-to-use liquid formulation suitable for parenteral administration.

In some embodiments of this aspect, the concentration of the phosphaplatin compound is about 20 mg/mL or less.

In some embodiments of this aspect, the concentration of the phosphaplatin compound is between about 1 and about 10 mg/mL.

In some embodiments of this aspect, the concentration of the phosphaplatin compound is between about 1 and about 6 mg/mL.

In another embodiment of this aspect, the concentration of the phosphaplatin compound is about 5 mg/mL.

In another embodiment of this aspect, the buffer comprises a salt of phosphate or bicarbonate/carbonate.

In some embodiments, the buffer comprises phosphate family ions, i.e., phosphate ($PO_4^{3-}$), hydrogen phosphate ($HPO_4^{2-}$), and/or dihydrogen phosphate ($H_2PO_4^-$).

In some embodiments, the buffer comprises carbonate family ions, i.e, bicarbonate ($HCO_3^-$) and carbonate ($CO_3^{2-}$).

In some embodiments, the buffer comprises both phosphate family ions ($PO_4^{3-}$, $HPO_4^{2-}$, and/or $H_2PO_4^-$ ions) and carbonate family ions (i.e., $HCO_3^-$ and $CO_3^{2-}$).

In some embodiments of this aspect, the buffer salt concentration is between about 1 mM and about 100 mM.

In some embodiments of this aspect, the buffer salt concentration is between about 5 mM and about 50 mM.

In some embodiments of this aspect, the buffer salt concentration is about 10 mM.

In some embodiments of this aspect, the pH of the liquid pharmaceutical composition is in the range of about 7.0 to about 9.0.

In some embodiments of this aspect, the pH of the liquid pharmaceutical composition is in the range of about 7.0 to about 8.0.

In some embodiments of this aspect, the buffer contains sodium or potassium phosphate salts, or a combination thereof.

In some embodiments of this aspect, the buffer contains potassium phosphate; the concentration of the phosphaplatin compound is 5 mg/mL and the pH is in the range of about 7.0 to about 8.0.

In some embodiments of this aspect, the buffer concentration is about 10 mM.

In some embodiments of this aspect, the buffer comprises a pyrophosphate salt.

In some embodiments of this aspect, the molar ratio of pyrophosphate anion to the phosphaplatin compound is at least 0.1 to 1.

In some embodiments of this aspect, the molar ratio of pyrophosphate ion to the phosphaplatin compound is about 0.2 to 1 In some embodiments of this aspect, the molar ratio of pyrophosphate ion to the phosphaplatin compound is about 0.4 to 1.

In some embodiments of this aspect, the concentration of the phosphaplatin compound is about 5 mg/mL, the pyrophosphate concentration is about 5.2 mM, and the pH is in the range of about 7.0 to about 8.0.

In some embodiments of this aspect, the phosphaplatin compound is a pyrophosphato-platinum (II) complex having a formula of (I) or (II):

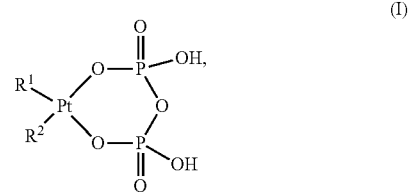

(I)

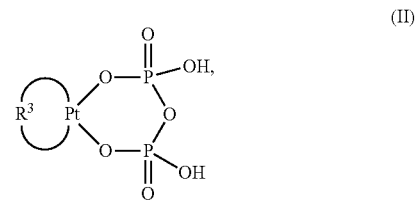

(II)

or a salt thereof, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic or aromatic 1,2-diamines.

In some preferred embodiments, $R^1$ and $R^2$ in formula (I) are each independently selected from $NH_3$, methyl amine, ethyl amine, propyl amine, isopropyl amine, butyl amine, cyclohexane amine, aniline, pyridine, and substituted pyridine; and $R^3$ in formula (II) is selected from ethylenediamine and cyclohexanediamine.

In some more preferred embodiments of this aspect, the phosphaplatin compound is a 1,2-cyclohexanediamine-(dihydrogen pyrophosphato)platinum(II) ("pyrodach-2") complex selected from the group consisting of:

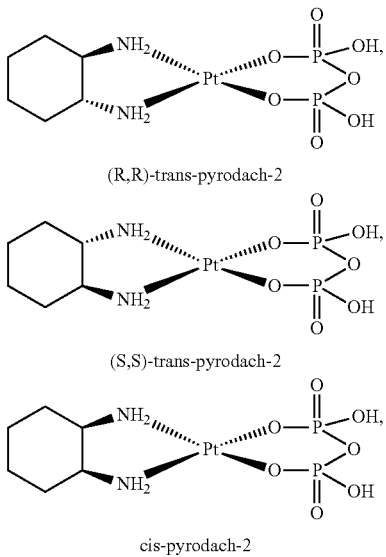

(R,R)-trans-pyrodach-2

(S,S)-trans-pyrodach-2 cis-pyrodach-2

In one preferred embodiment of this aspect, the phosphaplatin compound is a trans-1,2-cyclohexanediamine-(dihydrogen pyrophosphato)platinum(II) ("trans-pyrodach-2") complex.

In another preferred embodiment of this aspect, the phosphaplatin compound is (R,R)-trans-1,2-cyclohexanediamine-(dihydrogen pyrophosphato)platinum(II) ("(R,R)-trans-pyrodach-2").

In another preferred embodiment of this aspect, the phosphaplatin compound is (S,S)-trans-1,2-cyclohexanediamine-(dihydrogen pyrophosphato)platinum(II) ("(S,S)-trans-pyrodach-2").

In another preferred embodiment of this aspect, the phosphaplatin compound is cis-1,2-cyclohexanediamine-(dihydrogen pyrophosphato)-platinum(II) ("cis-pyrodach-2").

In some embodiments, the present invention provides liquid pharmaceutical compositions of phosphaplatin according to any reasonable combinations of the embodiments described herein.

In another aspect, the present invention provides a liquid pharmaceutical composition according to any embodiment disclosed herein, or any combination thereof, for use in the treatment of a disease or disorder.

In some embodiments, the disease or disorder is a cancer.

In some embodiments, the cancer includes, but is not limited to, those selected from gynecological cancers, genitourinary cancers, lung cancers, head-and-neck cancers, skin cancers, gastrointestinal cancers, breast cancers, bone and chondroital cancers, and hematological cancers.

In some embodiments, the cancer is selected from the group consisting of ovarian cancer, testicular cancer, small-cell lung cancer, non-small-cell lung cancer, head-and-neck cancers, skin cancer, pancreatic cancer, breast cancer, liver cancer, stomach cancer, bone cancer, glioblastoma cancer, and colon cancer.

In another aspect, the present invention provides use of a liquid pharmaceutical composition according to any embodiment disclosed herein, or any combination thereof, for use in the manufacture of a medicament for the treatment of a disease or disorder. The disease or disorder includes a cancer, including but not limited to any of gynecological cancers, genitourinary cancers, lung cancers, head-and-neck cancers, skin cancers, gastrointestinal cancers, breast cancers, bone and chondroital cancers, and hematological cancers. More specific non-limiting examples include ovarian cancer, testicular cancer, small-cell lung cancer, non-small-cell lung cancer, head-and-neck cancers, skin cancer, pancreatic cancer, breast cancer, liver cancer, stomach cancer, bone cancer, glioblastoma cancer, and colon cancer.

In another aspect, the present invention provides a process of preparing a liquid pharmaceutical composition of phosphaplatin compound according to any embodiments disclosed herein, or any combination thereof, the process comprises: a) dissolving a phosphaplatin compound in an aqueous buffer comprising a sufficient amount of hydroxide base such that the pH remains at or above 7; b) optionally adding a hydroxide base to adjust the pH to a desired range, and c) filtering the solution to obtain a liquid formulation.

In one embodiment of this aspect, the aqueous buffer is a phosphate buffer, a carbonate/biocarbonate buffer, or a combination thereof.

In another embodiment of this aspect, the pH of the liquid formulation is in the range of about 7.0 to about 9.0.

In another embodiment of this aspect, the process further includes adding a sufficient amount of a pyrophosphate salt to stabilize the phosphaplatin compound in the liquid formulation.

In another embodiment of this aspect, said filtering is conducted under sterile conditions.

In another embodiment of this aspect, the process further comprises step d) filling the solution into a vial, stoppering and capping the vial in a sterile environment so that the formulation is ready for use.

In another embodiment of this aspect, the liquid formulation obtained is a formulation according to any one of the embodiments described herein, or any combination thereof.

When the term "about" is applied to a parameter, such as pH, concentration, or the like, it indicates that the parameter can vary by ±10%, preferably within ±5%, and more preferably within ±5%. As would be understood by a person skilled in the art, when a parameter is not critical, a number is often given only for illustration purpose, instead of being limiting.

The term "a," "an," or "the," as used herein, represents both singular and plural forms. In general, when either a singular or a plural form of a noun is used, it denotes both singular and plural forms of the noun.

The present invention is equally applicable to all of the stereoisomers of pyrodach-2 complexes, as a person skilled in the art would understand, though the following detailed description uses only the (R,R)-pyrodach-2 isomer (or "PT-112") as a non-limiting example to illustrate certain aspects of the present invention.

(R,R)-Pyrodach-2 is a diacid, which displays a low solubility in water. The pKa values of the two acid groups in (R,R)-pyrodach-2 are approximately 2.6 and 4.4 (*Inorg. Chem.* 47, 7942 (2008)). Thus, simple dissolution of (R,R)-pyrodach-2 affords an acidic solution. Under acidic aqueous conditions (R,R)-pyrodach-2 rapidly undergoes hydrolytic degradation. At higher pHs, where the acid groups of (R,R)-pyrodach-2 are ionized, the solubility of (R,R)-pyrodach-2 increases. In addition, deprotonation of the acid groups in (R,R)-pyrodach-2 dramatically reduces the rate of hydrolytic degradation. The two pKa values of (R,R)-pyrodach-2 indicate that an aqueous solution of (R,R)-pyrodach-2 in the physiological pH range of 7.0-7.5 will have no buffering capacity. Thus, controlling the pH of an aqueous solution in the physiological pH range, much less the accurate and reproducible preparation of aqueous (R,R)-pyrodach-2 solutions in this pH range by pH adjustment of an aqueous solution of (R,R)-pyrodach-2 with hydroxide base, is extremely difficult. Hence, the development of aqueous formulations of (R,R)-pyrodach-2 with controlled pH stability in the physiological pH range of 7-7.5 preferably requires the use of a buffer. This presents a unique challenge as the pyrophosphate ligand in (R,R)-pyrodach-2 is kinetically labile in solution and can potentially undergo reaction with anions present in many buffers. Table 1 summarizes the decrease in potency measured by HPLC of aqueous 1 mg/mL (R,R)-pyrodach-2 solutions in a variety of buffers at ambient temperature. The HPLC system and conditions used to monitor stability are summarized in Table 2.

TABLE 1

| Buffer | Buffer conc. (mM) | pH | Decrease in Potency | | | |
|---|---|---|---|---|---|---|
| | | | 4 days | 7 days | 11 days | 14 days |
| Acetate | 20 mM | 5.32 | — | 13.5% | — | — |
| Citric acid | 20 mM | 6.51 | 1.9% | — | 3.9% | — |
| Triethanolamine | 20 mM | 7.97 | 1.9% | — | 5.7% | — |
| L-arginine | 20 mM | 7.72 | 4.0% | — | 10% | — |
| NH$_4$HCO$_3$ | 100 mM | 7.94 | — | — | — | 47.1% |
| NH$_4$HCO$_3$ | 50 mM | 7.83 | — | — | — | 18.0% |
| NH$_4$HCO$_3$ | 20 mM | 7.68 | | | | 8.0% |

TABLE 2

| Column | Waters Symmetry C18, 4.6 × 250 mm, 5 μm particle size |
|---|---|
| Column temperature | Ambient |
| Flow rate | 1 mg/mL |
| Injection volume | 25 μL |
| Mobile Phase | 15% Acetonitrile/85% 5 mM Tetrabutylammonium hydrogen sulfate + 10 mM Na$_2$HPO$_4$ |
| Detection | UV |

To develop a stable ready-to-use aqueous formulation of (R,R)-pyrodach-2 with a pH controlled in the range of 7.0-8.0, screening of buffers for their lack of reactivity towards (R,R)-pyrodach-2 in an aqueous solution resulted in identification of phosphate and bicarbonate/carbonate buffers as most preferable. Temperature was observed to impact stability, with poorer stability observed at higher temperatures. Buffer concentration was also found to impact (R,R)-pyrodach-2 solution stability, with poorer stability observed at higher buffer concentrations; while impact of the cation associated with the buffer (e.g., potassium vs. sodium, etc.) was found to be minimal, if any. In a bicarbonate/carbonate buffer system, pH was found to have a significant impact on (R,R)-pyrodach-2 stability, with decreased stability observed at a higher pH, where the concentration ratio of carbonate ion to bicarbonate ion increases. In contrast, in phosphate buffers, pH was found to have minimal impact on (R,R)-pyrodach-2 stability when the pH was above 7. Below pH 7, degradation was observed to result in formation of a dimeric species ((R,R)-pyrodach-2 dimer), which is highly insoluble and precipitates from the solution. Given the potential for degradation in the presence of carbonate ion in a bicarbonate/carbonate buffer system and for the potential loss in buffer capacity due to equilibration with CO$_2$ in the atmosphere or head space of a container, phosphate offers a superior buffering system for manufacture of a buffered aqueous ready-to-use (R,R)-pyrodach-2 formulation with the pH controlled in the physiological range of 7-7.5, particularly in a large scale manufacturing setting.

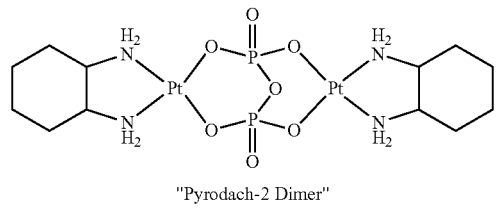

"Pyrodach-2 Dimer"

Freezing an aqueous formulation is one way to retard the rate of degradation and improve the stability of a drug substance formulated in aqueous media. The impact of a freeze-thaw cycle on the stability of (R,R)-pyrodach-2 in a variety of buffers was evaluated.

Data summarized in Table 3 shows a higher level of degradation with higher buffer concentrations. In addition, a higher level of degradation is observed with the sodium salt in comparison to the potassium salt in the phosphate buffer systems in consistence with the observation of selective precipitation of disodium phosphate during freezing, which results in a significant decrease in pH during freezing, a phenomenon not observed on a potassium phosphate buffer (Archives of Biochemistry and Biophysics 384, 398, 2000). Hence, use of potassium salts is preferable to use of sodium salts in phosphate buffered (R,R)-pyrodach-2 formulations.

TABLE 3

| 1 mg/mL (R,R)-pyrodach-2 solution in | Solution pH | Change in purity after freeze thaw cycle |
|---|---|---|
| 10 mM Na Phosphate | 7.02 | 99.5% |
| 10 mM Na Phosphate | 6.98 | 96.3% |

| 1 mg/mL (R,R)-pyrodach-2 | Solution pH | Change in |
|---|---|---|
| 10 mM K Phosphate | 7.01 | 99.7% |
| 10 mM K Phosphate | 7.02 | 99.1% |
| 10 mM Na Carbonate | 10.84 | 99.1% |
| 10 mM Na Carbonate | 11.39 | 93.7% |
| 10 mM Na Bicarbonate | 8.18 | 99.5% |
| 10 mM Na Bicarbonate | 8.06 | 98.8% |

The solubility of (R,R)-pyrodach-2 in aqueous buffered solution at pH 7-7.5 indicates that solutions of at least 20 mg/mL can easily be achieved. However, the clinical use of platinum oncolytic agents like (R,R)-pyrodach-2 indicates that a concentration of 5 mg/mL is highly desirable for a ready-to-use aqueous formulation. Buffering capacity modeling shows that a 10 mM concentration of phosphate or bicarbonate provides sufficient buffering capacity and acceptable pH control for a 5 mg/mL (R,R)-pyrodach-2 aqueous solution.

The rapid hydrolytic degradation of (R,R)-pyrodach-2, in particular the formation of the highly insoluble dimeric impurity both on dissolution of (R,R)-pyrodach-2 in water or in a buffer medium such as phosphate buffer when the pH is below neutral, precludes large scale manufacture of an aqueous ready-to-use formulation of (R,R)-pyrodach-2, adjusted to the physiological pH range of 7-7.5, by simply adding base to a slurry of (R,R)-pyrodach-2 in water or adding a buffer solution to effect dissolution followed by adjustment to the desired pH range. Rather, effective control of degradation and impurity formation requires dissolution of the (R,R)-pyrodach-2 under conditions of near neutral or basic pH. We have found that this can be achieved by adding (R,R)-pyrodach-2 to a solution of buffer and adding hydroxide base sufficient to neutralize all of the added (R,R)-pyrodach-2. Once all of the solids have dissolved, the solution pH is adjusted into the final desired range by the addition of small amount of hydroxide. In this manner the dissolution of the drug substance is conducted under conditions of near neutral or basic pH.

A scalable and commercially viable process for the manufacture of a ready-to-use formulation of (R,R)-pyrodach-2 in 10 mM buffer adjusted to a pH of 7.0-7.5 comprises the steps of: a) preparing a 10 mM aqueous solution of buffer; b) adding sufficient hydroxide base to effect neutralization of the added (R,R)-pyrodach-2 to reach a pH of about 7; c) adding (R,R)-pyrodach-2 and allowing it to dissolve; d) if necessary adding additional hydroxide to adjust the pH into a range of about 7.0-7.5; and e) filtering the solution under sterile conditions, filling the solution into glass vials, and covering it with a stopper and/or a cap. Stability data on two large batches of 5 mg/mL (R,R)-pyrodach-2 in 10 mM potassium phosphate buffer were generated. One such batch at pH=7.2 was evaluated at both 25° C./60% RH and refrigerated (2-8° C.) conditions, with data summarized in Table 4 and Table 5, respectively. While slow degradation is observed over 24 months at 25° C./60RH, under refrigerated conditions the formulation displays excellent stability over the same or even longer (36 months) period (see Table 5). Similar observations have been made for the ready-to-use liquid formulation at pH7.4, as illustrated in Table 6 and Table 7.

TABLE 4

(R,R)-Pyrodach-2 Ready-to-use Aqueous Formulation Stability at 25° C./60% RH (5 mg/mL (R,R)-pyrodach-2 in 10 mM Potassium Phosphate Buffer at pH 7.2) filled in 10 mL vials

| Parameter | Initial | 1 Month | 2 Month | 3 Month | 4 Month | 6 Month |
|---|---|---|---|---|---|---|
| Appearance | Clear, colorless solution free of particulates | Clear, colorless solution free of particulates | Clear, colorless solution free of particulates | Clear, colorless solution free of particulates | Clear, colorless solution free of particulates | Clear, colorless solution free of particulates |
| Assay (Potency) | 99.8% | 96.5% | 99.5% | 98.2% | 97.9% | 97.5% |
| Total Related Substances | 2% | 2% | 2% | 2% | 2% | 3% |
| (DACH) Pt-diaquo (~RRT 0.3) | 0.16% | 0.15% | 0.09% | 0.19% | 0.13% | 0.15% |
| (DACH) Pt-monoaquo (~RRT 0.7) | 0.98% | 0.75% | 0.96% | 0.73% | 1.05% | 1.03% |
| (DACH) Pt-dichloride (RRT 1.3-1.6) | ND | ND | ND | ND | ND | ND |
| RRT 3.1-3.2 | ND | 0.22% | 0.32% | 0.37% | 0.38% | 0.40% |
| PT-112 Dimer (~RRT 4.0) | 0.19% | 0.33% | 0.36% | 0.37% | 0.36% | 0.37% |
| RRT 0.41 | ND | ND | ND | ND | ND | ND |
| RRT 0.46 | ND | ND | ND | ND | ND | ND |
| RRT 0.50 | ND | ND | 0.05% | 0.08% | 0.09% | 0.15% |
| RRT 0.58 | 0.13% | 0.13% | 0.15% | 0.18% | 0.20% | 0.21% |
| RRT 0.67 | 0.05% | 0.06% | 0.09% | 0.06% | 0.07% | 0.07% |
| RRT 0.86 | ND | ND | ND | ND | ND | 0.05% |
| RRT 3.46 | ND | ND | ND | ND | 0.05% | ND |
| RRT 3.65 | ND | ND | 0.08% | 0.11% | 0.13% | 0.24% |
| RRT 4.97 | ND | ND | ND | ND | ND | 0.05% |
| pH | 7.2 | 7.2 | 7.2 | 7.3 | 7.1 | 7.2 |
| Sterility | Sterile | NT | NT | NT | NT | Sterile |
| Particulate Matter (Light Obscuration)[1] | 219 particles per container | NT | NT | NT | NT | 20 particles per container |
| | 11 particles per container | NT | NT | NT | NT | 3 particles per container |
| Bacterial Endotoxin (Kinetic Turbidimetric) | <0.35 EU/mL | NT | NT | NT | NT | <0.35 EU/mL |

| Parameter | Initial | 9 Month | 12 Month | 15 Month | 18 Month | 24 Month |
|---|---|---|---|---|---|---|
| Appearance | Clear, colorless solution free of particulates | Clear, colorless solution free of particulates | Clear, colorless solution free of particulates | Clear, colorless solution free of particulates | Clear, colorless solution free of particulates | Clear, colorless solution free of particulates |

TABLE 4-continued (R,R)-Pyrodach-2 Ready-to-use Aqueous Formulation Stability at 25° C./60% RH (5 mg/mL (R,R)-pyrodach-2 in 10 mM Potassium Phosphate Buffer at pH 7.2) filled in 10 mL vials

| | | | | | | |
|---|---|---|---|---|---|---|
| Assay (Potency) | 99.8% | 96.8% | 96.8% | 98.1% | 99.0% | 97.5% |
| Total Related Substances | 2% | 3% | 3% | 3% | 4% | 5% |
| (DACH) Pt-diaquo (~RRT 0.3) | 0.16% | 0.16% | 0.18% | 0.14% | 0.14% | 0.15% |
| (DACH) Pt-monoaquo (~RRT 0.7) | 0.98% | 1.10% | 0.91% | 0.84% | 1.04% | 0.83% |
| (DACH) Pt-dichloride (RRT 1.3-1.6) | ND | ND | ND | ND | ND | ND |
| RRT 3.1-3.2 | ND | 0.30% | 0.44% | 0.41% | 0.40% | 0.41% |
| PT-112 Dimer (~RRT 4.0) | 0.19% | 0.39% | 0.33% | 0.29% | 0.30% | 0.36% |
| RRT 0.41 | ND | ND | 0.05% | 0.07% | 0.06% | 0.12% |
| RRT 0.46 | ND | ND | ND | ND | ND | 0.10% |
| RRT 0.50 | ND | 0.19% | 0.26% | 0.37% | 0.36% | 0.70% |
| RRT 0.58 | 0.13% | 0.27% | 0.26% | 0.26% | 0.29% | 0.17% |
| RRT 0.67 | 0.05% | 0.10% | 0.13% | 0.07% | 0.11% | 0.07% |
| RRT 0.86 | ND | 0.05% | 0.05% | ND | 0.14% | ND |
| RRT 3.46 | ND | ND | ND | ND | ND | 0.07% |
| RRT 3.65 | ND | 0.39% | 0.52% | 0.63% | 0.75% | 1.24% |
| RRT 4.97 | ND | 0.08% | 0.20% | 0.28% | 0.43% | 0.73% |
| pH | 7.2 | 7.2 | 7.2 | 7.3 | 7.2 | 7.2 |
| Sterility | Sterile | NT | Sterile | NT | NT | Sterile |
| Particulate Matter (Light Obscuration) | 219 particles per container | NT | 36 particles per container | NT | NT | 81 particles per container |
| | 11 particles per container | NT | 2 particles per container | NT | NT | 4 particles per container |
| Bacterial Endotoxin (Kinetic Turbidimetric) | <0.35 EU/mL | NT | <0.35 EU/mL | NT | NT | <0.35 EU/mL |

ND = Not detected;
NT = Not tested

TABLE 5

(R,R)-Pyrodach-2 Ready-to-use Aqueous Formulation Stability 2-8° C. (5 mg/mL (R,R)-pyrodach-2 in 10 mM Potassium Phosphate Buffer at pH 7.2) filled in 10 mL vials

| Parameter | Initial | 1 Month | 2 Month | 3 Month | 4 Month | 6 Month | 9 Month |
|---|---|---|---|---|---|---|---|
| Appearance | Clear, colorless solution free of particulates | Clear, colorless solution free of particulates | Clear, colorless solution free of particulates | Clear, colorless solution free of particulates | Clear, colorless solution free of particulates | Clear, colorless solution free of particulates | Clear, colorless solution free of particulates |
| Assay (Potency) | 99.8% | 97.7% | 100.1% | 98.2% | 98.6% | 98.4% | 97.8% |
| Total Related Substances | 2% | 1% | 1% | 2% | 2% | 2% | 2% |
| (DACH) Pt-diaquo (~RRT 0.3) | 0.16% | 0.17% | 0.09% | 0.18% | 0.13% | 0.18% | 0.14% |
| (DACH) Pt-monoaquo (~RRT 0.7) | 0.98% | 0.84% | 0.91% | 0.82% | 0.88% | 0.91% | 1.05% |
| (DACH) Pt-dichloride (RRT 1.3-1.6) | ND | ND | ND | ND | ND | ND | ND |
| RRT 3.1-3.2 | ND | ND | ND | 0.08% | 0.07% | 0.10% | 0.10% |
| PT-112 Dimer (~RRT 4.0) | 0.19% | 0.21% | 0.25% | 0.31% | 0.27% | 0.28% | 0.29% |
| RRT 0.46 | ND | ND | ND | ND | ND | ND | ND |
| RRT 0.50 | ND | ND | ND | ND | 0.05% | ND | ND |
| RRT 0.56 | 0.13% | 0.11% | 0.10% | 0.12% | 0.13% | 0.12% | 0.16% |
| RRT 0.68 | 0.05% | ND | 0.06% | 0.05% | ND | 0.05% | 0.06% |
| RRT 3.54 | ND | ND | ND | ND | ND | ND | ND |
| pH | 7.2 | 7.2 | 7.2 | 7.2 | 7.3 | 7.3 | 7.2 |
| Sterility | Sterile | NT | NT | NT | NT | Sterile | NT |
| Particulate Matter | 219 | NT | NT | NT | NT | 150 | NT |

TABLE 5-continued (R,R)-Pyrodach-2 Ready-to-use Aqueous Formulation Stability 2-8° C. (5 mg/mL (R,R)-pyrodach-2 in 10 mM Potassium Phosphate Buffer at pH 7.2) filled in 10 mL vials

| | | | | | | | |
|---|---|---|---|---|---|---|---|
| (Light Obscuration) | particles per container 11 particles per container | NT | NT | NT | NT | particles per container 8 particles per container | NT |
| Bacterial Endotoxin (Kinetic Turbidimetric) | <0.35 EU/mL | NT | NT | NT | NT | <0.35 EU/mL | NT |

| Parameter | Initial | 12 Month | 15 Month | 18 Month | 24 Month | 30 Month | 36 Month |
|---|---|---|---|---|---|---|---|
| Appearance | Clear, colorless solution free of particulates | Clear, colorless solution free of particulates | Clear, colorless solution free of particulates | Clear, colorless solution free of particulates | Clear, colorless solution free of particulates | Clear, colorless solution free of particulates | Clear, colorless solution free of particulates |
| Assay (Potency) | 99.8% | 97.8% | 98.7% | 100.3% | 97.1% | 98.2% | 97.8% |
| Total Related Substances | 2% | 2% | 2% | 2% | 2% | 2% | 3% |
| (DACH) Pt-diaquo (~RRT 0.3) | 0.16% | 0.20% | 0.15% | 0.15% | 0.17% | 0.14% | 0.12% |
| (DACH) Pt-monoaquo (~RRT 0.7) | 0.98% | 1.02% | 0.92% | 0.93% | 0.82% | 0.96% | 1.16% |
| (DACH) Pt-dichloride (RRT 1.3-1.6) | ND | ND | ND | ND | ND | ND | ND |
| RRT 3.1-3.2 | ND | 0.16% | 0.22% | 0.19% | 0.22% | 0.31% | 0.30% |
| PT-112 Dimer (~RRT 4.0) | 0.19% | 0.29% | 0.29% | 0.31% | 0.31% | 0.33% | 0.36% |
| RRT 0.46 | ND | ND | ND | ND | 0.06% | ND | 0.07% |
| RRT 0.50 | ND | 0.06% | 0.07% | 0.07% | 0.22% | 0.17% | 0.23% |
| RRT 0.56 | 0.13% | 0.16% | 0.19% | 0.19% | 0.09% | 0.19% | 0.11% |
| RRT 0.68 | 0.05% | 0.10% | 0.06% | 0.07% | 0.05% | 0.08% | 0.09% |
| RRT 3.54 | ND | ND | ND | 0.05% | 0.11% | 0.10% | 0.14% |
| pH | 7.2 | 7.2 | 7.2 | 7.3 | 7.2 | 7.2 | 7.2 |
| Sterility | Sterile | Sterile | NT | NT | Sterile | Sterile | NT |
| Particulate Matter (Light Obscuration) | 219 particles per container 11 particles per container | 236 particles per container 4 particles per container | NT | NT | 41 particles per container 12 particles per container | 62 particles per container 6 particles per container | NT |
| Bacterial Endotoxin (Kinetic Turbidimetric) | <0.35 EU/mL | <0.35 EU/mL | NT | NT | <0.35 EU/mL | <0.35 EU/mL | NT |

ND = Not detected;
NT = Not tested

TABLE 6

(R,R)-Pyrodach-2 Ready-to-use Aqueous Formulation Stability at 25° C./60% RH (5 mg/mL (R,R)-pyrodach-2 in 10 mM Potassium Phosphate Buffer at pH 7.4) filled in 10 mL vials

| Parameter | Initial | 1 Month | 3 Month | 6 Month | 9 Month | 12 Month |
|---|---|---|---|---|---|---|
| Appearance | Clear, colorless solution free of particulates | Clear, colorless solution free of particulates | Clear, colorless solution free of particulates | Clear, colorless solution free of particulates | Clear, colorless solution free of particulates | Clear, colorless solution free of particulates |
| Assay (Potency) | 98.1% | 98.4% | 99.2% | 96.7% | 98.2% | 98.0% |
| Total Related Substances | 2% | 3% | 3% | 3% | 4% | 4% |
| (DACH) Pt-diaquo (~RRT 0.3) | 0.16% | 0.16% | 0.15% | 0.19% | 0.14% | 0.11% |
| (DACH) Pt-monoaquo (~RRT 0.7) | 0.84% | 1.12% | 0.92% | 0.30% | 0.79% | 0.92% |

TABLE 6-continued (R,R)-Pyrodach-2 Ready-to-use Aqueous Formulation Stability at 25° C./60% RH (5 mg/mL
(R,R)-pyrodach-2 in 10 mM Potassium Phosphate Buffer at pH 7.4) filled in 10 mL vials

| | | | | | | |
|---|---|---|---|---|---|---|
| (DACH) Pt-dichloride (RRT 1.3-1.6) | ND | ND | ND | ND | ND | ND |
| RRT 3.1-3.2 | 0.11% | 0.56% | 0.77% | 0.86% | 0.84% | 0.82% |
| PT-112 Dimer (~RRT 4.0) | 0.34% | 0.35% | 0.33% | 0.36% | 0.34% | 0.30% |
| RRT 0.42 | ND | ND | ND | 0.06% | 0.08% | 0.10% |
| RRT 0.46 | ND | ND | ND | 0.09% | 0.08% | 0.07% |
| RRT 0.50 | 0.06% | 0.07% | 0.11% | 0.31% | 0.39% | 0.38% |
| RRT 0.56 | 0.08% | 0.15% | 0.20% | 0.09% | 0.11% | 0.19% |
| RRT 0.68 | 0.09% | 0.21% | 0.11% | 0.16% | 0.11% | 0.11% |
| RRT 0.86 | ND | 0.06% | 0.05% | 0.07% | 0.06% | 0.05% |
| RRT 3.29 | ND | ND | ND | ND | ND | ND |
| RRT 3.41 | ND | ND | ND | ND | 0.08% | ND |
| RRT 3.44 | ND | ND | ND | ND | ND | ND |
| RRT 3.58 | ND | ND | 0.14% | 0.37% | 0.65% | 0.70% |
| RRT 4.95 | ND | ND | ND | 0.06% | 0.21% | 0.34% |
| pH | 7.4 | 7.4 | 7.4 | 7.4 | 7.4 | 7.5 |
| Sterility | Sterile | NT | NT | Sterile | NT | Sterile |
| Particulate Matter (Light Obscuration)[1] | 30 particles per container | NT | NT | 87 particles per container | NT | 118 particles per container |
| | 11 particles per container | NT | NT | 3 particles per container | NT | 7 particles per container |
| Bacterial Endotoxin (Kinetic Turbidimetric)[1] | <0.35 EU/mL | NT | NT | <0.35 EU/mL | NT | <0.35 EU/mL |

| Parameter | Initial | 15 Month | 18 Month | 21 Month | 24 Month |
|---|---|---|---|---|---|
| Notebook Reference | 1245-6-46 | 1245-14-36 | 1245-14-49 | 1245-14-59 | 1245-14-76 |
| Appearance | Clear, colorless solution free of particulates | Clear, colorless solution free of particulates | Clear, colorless solution free of particulates | Clear, colorless solution free of particulates | Clear, colorless solution free of particulates |
| Assay (Potency) | 98.1% | 96.8% | 96.9% | 96.3% | 94.6% |
| Total Related Substances | 2% | 4% | 5% | 6% | 6% |
| Individual Related Substances | | | | | |
| (DACH) Pt-diaquo (~RRT 0.3) | 0.16% | 0.13% | 0.12% | 0.11% | 0.11% |
| (DACH) Pt-monoaquo (~RRT 0.7) | 0.84% | 0.92% | 0.78% | 1.13% | 0.85% |
| (DACH) Pt-dichloride (RRT 1.3-1.6) | ND | ND | ND | ND | ND |
| RRT 3.1-3.2 | 0.11% | 0.78% | 0.73% | 0.75% | 0.72% |
| PT-112 Dimer (~RRT 4.0) | 0.34% | 0.28% | 0.29% | 0.28% | 0.28% |
| RRT 0.42 | ND | 0.12% | 0.15% | 0.16% | 0.18% |
| RRT 0.46 | ND | 0.08% | 0.13% | 0.12% | 0.12% |
| RRT 0.50 | 0.06% | 0.44% | 0.59% | 0.60% | 0.70% |
| RRT 0.56 | 0.08% | 0.20% | 0.09% | 0.17% | 0.17% |
| RRT 0.68 | 0.09% | 0.11% | 0.08% | 0.12% | 0.13% |
| RRT 0.86 | ND | 0.05% | 0.05% | ND | 0.05% |
| RRT 3.29 | ND | ND | ND | ND | 0.06% |
| RRT 3.41 | ND | ND | ND | 0.07% | ND |
| RRT 3.44 | ND | ND | 0.12% | 0.05% | 0.05% |
| RRT 3.58 | ND | 0.78% | 1.06% | 1.12% | 1.07% |
| RRT 4.95 | ND | 0.51% | 0.69% | 0.89% | 1.12% |
| pH | 7.4 | 7.5 | 7.5 | 7.4 | 7.4 |
| Sterility | Sterile | NT | NT | NT | TBD |
| Particulate Matter (Light Obscuration) | 30 particles per container | NT | NT | NT | TBD |
| | 11 particles per container | NT | NT | NT | TBD |
| Bacterial Endotoxin (Kinetic Turbidimetric) | <0.35 EU/mL | NT | NT | NT | TBD |

TABLE 7

(R,R)-Pyrodach-2 Ready-to-use Aqueous Formulation Stability at 2-8° C. (5 mg/mL (R,R)-pyrodach-2 in 10 mM Potassium Phosphate Buffer at pH 7.4) filled in 10 mL vials

| Parameter | Initial | 1 Month | 3 Month | 6 Month | 9 Month | 12 Month |
|---|---|---|---|---|---|---|
| Appearance | Clear, colorless solution free of particulates | Clear, colorless solution free of particulates | Clear, colorless solution free of particulates | Clear, colorless solution free of particulates | Clear, colorless solution free of particulates | Clear, colorless solution free of particulates |
| Assay (Potency) | 98.1% | 98.7% | 99.7% | 98.2% | 100.2% | 98.7% |
| Total Related Substances | 2% | 2% | 2% | 2% | 2% | 2% |
| (DACH) Pt-diaquo (~RRT 0.3) | 0.16% | 0.15% | 0.14% | 0.17% | 0.14% | 0.12% |
| (DACH) Pt-monoaquo (~RRT 0.7) | 0.84% | 1.04% | 0.92% | 0.28% | 0.81% | 0.96% |
| (DACH) Pt-dichloride (RRT 1.3-1.6) | ND | ND | ND | ND | ND | ND |
| RRT 3.1-3.2 | 0.11% | 0.13% | 0.25% | 0.38% | 0.39% | 0.48% |
| PT-112 Dimer (~RRT 4.0) | 0.34% | 0.33% | 0.37% | 0.36% | 0.33% | 0.34% |
| RRT 0.46 | ND | ND | ND | 0.06% | 0.05% | ND |
| RRT 0.50 | 0.06% | 0.06% | 0.06% | 0.18% | 0.18% | 0.15% |
| RRT 0.56 | 0.08% | 0.10% | 0.12% | 0.06% | 0.07% | 0.16% |
| RRT 0.68 | 0.09% | 0.19% | 0.11% | 0.16% | 0.08% | 0.11% |
| RRT 0.86 | ND | 0.05% | ND | 0.05% | 0.05% | 0.05% |
| RRT 3.58 | ND | ND | ND | ND | 0.07% | ND |
| pH | 7.4 | 7.4 | 7.4 | 7.4 | 7.4 | 7.4 |
| Sterility | Sterile | NT | NT | Sterile | NT | Sterile |
| Particulate Matter (Light Obscuration) | 30 particles per container | NT | NT | 83 particles per container | NT | 124 particles per container |
|  | 11 particles per container | NT | NT | 1 particles per container | NT | 6 particles per container |
| Bacterial Endotoxin (Kinetic Turbidimetric)[1] | <0.35 EU/mL | NT | NT | <0.35 EU/mL | NT | <0.35 EU/mL |

| Parameter | Initial | 15 Month | 18 Month | 21 Month | 24 Month |
|---|---|---|---|---|---|
| Appearance | Clear, colorless solution free of particulates | Clear, colorless solution free of particulates | Clear, colorless solution free of particulates | Clear, colorless solution free of particulates | Clear, colorless solution free of particulates |
| Assay (Potency) | 98.1% | 98.0% | 97.5% | 97.4% | 96.5% |
| Total Related Substances | 2% | 3% | 2% | 3% | 3% |
| (DACH) Pt-diaquo (~RRT 0.3) | 0.16% | 0.14% | 0.13% | 0.12% | 0.11% |
| (DACH) Pt-monoaquo (~RRT 0.7) | 0.84% | 0.94% | 0.76% | 1.07% | 0.93% |
| (DACH) Pt-dichloride (RRT 1.3-1.6) | ND | ND | ND | ND | ND |
| RRT 3.1-3.2 | 0.11% | 0.59% | 0.58% | 0.67% | 0.65% |
| PT-112 Dimer (~RRT 4.0) | 0.34% | 0.34% | 0.33% | 0.35% | 0.33% |
| RRT 0.46 | ND | ND | 0.09% | 0.07% | 0.08% |
| RRT 0.50 | 0.06% | 0.16% | 0.26% | 0.23% | 0.25% |
| RRT 0.56 | 0.08% | 0.17% | 0.06% | 0.12% | 0.12% |
| RRT 0.68 | 0.09% | 0.12% | 0.08% | 0.14% | 0.11% |

TABLE 7-continued (R,R)-Pyrodach-2 Ready-to-use Aqueous Formulation Stability at 2-8° C. (5 mg/mL (R,R)-pyrodach-2 in 10 mM Potassium Phosphate Buffer at pH 7.4) filled in 10 mL vials

| | | | | | |
|---|---|---|---|---|---|
| RRT 0.86 | ND | 0.06% | 0.05% | 0.05% | 0.06% |
| RRT 3.58 | ND | 0.07% | 0.10% | 0.10% | 0.14% |
| pH | 7.4 | 7.4 | 7.4 | 7.4 | 7.4 |
| Sterility | Sterile | NT | NT | NT | TBD |
| Particulate Matter (Light Obscuration) | 30 particles per container | NT | NT | NT | TBD |
| | 11 particles per container | NT | NT | NT | TBD |
| Bacterial Endotoxin (Kinetic Turbidimetric) | <0.35 EU/mL | NT | NT | NT | TBD |

ND = Not detected, or <0.05% area
NT = Not Tested

Stability data on a batch of 5 mg/mL (R,R)-pyrodach-2 in 10 mM bicarbonate buffer (pH 8.6) at 25° C./60% RH, 2-8° C. and −20° C. are summarized in Table 8, Table 9, and Table 10, respectively.

Surprisingly, the addition of a small amount of pyrophosphate ion has been found to dramatically improve the thermal stability of ready-to-use aqueous formulations of (R,R)-pyrodach-2. The addition not only retards the rate of degradation as a function of temperature, but it also serves to decrease the concentration of several impurities, including (DACH)Pt—$Cl_2$, an impurity which can be present in (R,R)-pyrodach-2 based on the route of manufacture (WO2013176764 A1), (R,R)-pyrodach-2 dimer, and the impurity that forms in (R,R)-pyrodach-2 formulated in phosphate buffer and elutes at RRT 3.1-3.2 in the HPLC system described in Example 3.

The ability of added pyrophosphate to reduce the concentration of (R,R)-pyrodach-2 dimer is particularly advantageous because this impurity is readily formed in aqueous solution of (R,R)-pyrodach-2 below 7, is highly insoluble, and can, at very low concentrations, precipitate from aqueous (R,R)-pyrodach-2 solutions. For example, in a 5 mg/mL ready-to-use formulation of (R,R)-pyrodach-2 manufactured according to Example 6 where the initial concentration of (R,R)-pyrodach-2 dimer was ~0.6 area %, the dimer was observed to begin to precipitate as a crystalline solid between 6 and 9 months of storage at 2-8° C., with crystallization observed in all sample vials by 12 months of storage.

TABLE 8

(R,R)-Pyrodach-2 Ready-to-use Aqueous Formulation Stability 25° C./60% RH
(5 mg/mL (R,R)-pyrodach-2 in 10 mM Bicarbonate Buffer at pH 8.6) filled in 10 mL vials

| Parameter | Initial | 1 week | 2 week | 3 week | 1 month | 2 month |
|---|---|---|---|---|---|---|
| Appearance | Clear solution with no visible particulates | Clear solution with no visible particulates | Clear solution with no visible particulates | Clear solution with no visible particulates | Clear solution with no visible particulates | Clear solution with no visible particulates |
| Potency (Assay) | 100.3% | 101.7% | 99.9% | 100.3% | 98.9% | 100.4% |
| Purity (% Area) | 98.04% | 97.74% | 97.77% | 97.33% | 97.44% | 96.45% |
| Unknown Impurities | | | | | | |
| RRT~0.29 | 0.11% | 0.11% | 0.12% | 0.16% | 0.16% | 0.19% |
| RRT~0.42 | ND | 0.05% | 0.10% | 0.15% | 0.21% | 0.56% |
| RRT~0.49 | 0.62% | 0.78% | 0.77% | 0.76% | 0.75% | 0.79% |
| RRT~0.59 | ND | 0.06% | ND | 0.12% | 0.15% | 0.26% |
| RRT~0.73 | 1.05% | 1.12% | 1.17% | 1.26% | 1.03% | 0.97% |
| RRT~1.82 | ND | ND | ND | ND | ND | ND |
| RRT~2.85 | ND | ND | ND | ND | ND | 0.12% |
| RRT~3.00 | ND | ND | ND | ND | ND | ND |
| RRT~3.15 | ND | ND | ND | ND | ND | ND |
| RRT~3.30 | ND | ND | ND | ND | ND | ND |
| RRT~3.45 | ND | ND | ND | ND | ND | 0.05% |
| RRT~3.74 | ND | ND | ND | 0.06% | 0.08% | 0.31% |
| RRT~4.27 | ND | ND | ND | ND | ND | ND |
| RRT~4.99 | ND | ND | ND | ND | ND | 0.07% |
| pH | 8.60 | 8.57 | 8.64 | 8.67 | 8.68 | 8.73 |
| Parameter | 3 month | 4 month | 6 month | 9 month | 12 month | |
| Appearance | Clear solution with no visible particulates | Clear solution with no visible particulates | Clear solution with no visible particulates | Clear solution with no visible particulates | Clear solution with no visible particulates | |

TABLE 8-continued (R,R)-Pyrodach-2 Ready-to-use Aqueous Formulation Stability 25° C./60% RH
(5 mg/mL (R,R)-pyrodach-2 in 10 mM Bicarbonate Buffer at pH 8.6) filled in 10 mL vials

| | | | | | |
|---|---|---|---|---|---|
| Potency (Assay) | 101.6% | 103.0% | 99.2% | 100.3% | 98.4% |
| Purity (% Area) | 96.08% | 95.98% | 95.03% | 93.82% | 92.23% |
| Unknown Impurities | | | | | |
| RRT~0.29 | 0.27% | 0.16% | 0.22% | 0.15% | 0.14% |
| RRT~0.42 | 0.76% | 0.96% | 1.29% | 1.88% | 2.20% |
| RRT~0.49 | 0.78% | 0.94% | 0.80% | 0.84% | 0.86% |
| RRT~0.59 | 0.25% | 0.17% | 0.32% | 0.32% | 0.32% |
| RRT~0.73 | 0.92% | 0.73% | 0.82% | 0.43% | 0.97% |
| RRT~1.82 | ND | ND | ND | 0.05% | 0.06% |
| RRT~2.85 | 0.17% | 0.17% | 0.15% | 0.32% | 0.37% |
| RRT~3.00 | ND | ND | 0.07% | ND | 0.06% |
| RRT~3.15 | ND | ND | ND | 0.07% | 0.06% |
| RRT~3.30 | ND | ND | 0.05% | 0.10% | 0.12% |
| RRT~3.45 | ND | ND | ND | 0.06% | 0.05% |
| RRT~3.74 | 0.40% | 0.58% | 0.69% | 0.88% | 1.07% |
| RRT~4.27 | 0.06% | 0.06% | 0.08% | 0.13% | 0.15% |
| RRT~4.99 | 0.14% | 0.20% | 0.36% | 0.66% | 1.02% |
| pH | 9.01 | 8.90 | 8.93 | 9.08 | 9.07 |

ND = Not Detected, or <0.05%;
NT = Not Tested;
RRT = Relative Retention time

TABLE 9

(R,R)-Pyrodach-2 Ready-to-use Aqueous Formulation Stability 2-8° C.
(5 mg/mL (R,R)-pyrodach-2 in 10 mM Bicarbonate Buffer at pH 8.6) filled in 10 mL vials

| Parameter | Initial | 1 week | 2 week | 3 week | 1 month | 2 month |
|---|---|---|---|---|---|---|
| Appearance | Clear solution with no visible particulates | Clear solution with no visible particulates | Clear solution with no visible particulates | Clear solution with no visible particulates | Clear solution with no visible particulates | Clear solution with no visible particulates |
| Potency (Assay) | 100.3% | 101.9% | 100.5% | 100.0% | 99.1% | 102.4% |
| Purity (% Area) | 98.04% | 98.02% | 97.99% | 97.91% | 97.85% | 97.58% |
| Unknown Impurities | | | | | | |
| RRT~0.29 | 0.11% | 0.10% | 0.12% | 0.14% | 0.14% | 0.21% |
| RRT~0.35 | ND | ND | ND | ND | ND | ND |
| RRT~0.41 | ND | ND | ND | ND | 0.05% | 0.11% |
| RRT~0.49 | 0.62% | 0.60% | 0.63% | 0.56% | 0.55% | 0.62% |
| RRT~0.59 | ND | ND | 0.06% | 0.07% | 0.08% | 0.15% |
| RRT~0.73 | 1.05% | 1.11% | 1.14% | 1.11% | 1.14% | 1.03% |
| RRT~1.51 | ND | ND | ND | ND | ND | ND |
| RRT~2.82 | ND | ND | ND | ND | ND | ND |
| RRT~3.44 | ND | ND | ND | ND | ND | 0.06% |
| pH | 8.60 | 8.57 | 8.65 | 8.67 | 8.73 | 8.76 |

| Parameter | 3 month | 4 month | 6 month | 9 month | 12 month |
|---|---|---|---|---|---|
| Appearance | Clear solution with no visible particulates | Clear solution with no visible particulates | Clear solution with no visible particulates | Clear solution with no visible particulates | Clear solution with no visible particulates |
| Potency (Assay) | 102.3% | 103.5% | 100.4% | 102.2% | 100.3% |
| Purity (% Area) | 97.76% | 98.07% | 97.56% | 97.73% | 96.64% |
| Unknown Impurities | | | | | |
| RRT~0.29 | 0.29% | 0.15% | 0.23% | 0.15% | 0.13% |
| RRT~0.35 | ND | ND | ND | ND | 0.05% |
| RRT~0.41 | 0.13% | 0.16% | 0.23% | 0.33% | 0.47% |
| RRT~0.49 | 0.53% | 0.68% | 0.65% | 0.58% | 0.64% |
| RRT~0.59 | 0.15% | 0.09% | 0.21% | 0.24% | 0.27% |
| RRT~0.73 | 0.89% | 0.72% | 0.90% | 0.43% | 0.98% |
| RRT~1.51 | 0.06% | 0.05% | ND | 0.05% | ND |

TABLE 9-continued (R,R)-Pyrodach-2 Ready-to-use Aqueous Formulation Stability 2-8° C.
(5 mg/mL (R,R)-pyrodach-2 in 10 mM Bicarbonate Buffer at pH 8.6) filled in 10 mL vials

| | | | | | |
|---|---|---|---|---|---|
| RRT~2.82 | 0.05% | 0.05% | ND | 0.13% | 0.19% |
| RRT~3.44 | ND | ND | 0.09% | 0.16% | 0.28% |
| pH | 8.95 | 8.83 | 8.84 | 9.07 | 8.97 |

ND = Not Detected, or <0.05%;
NT = Not Tested;
RRT = Relative Retention time

TABLE 10

(R,R)-Pyrodach-2 Ready-to-use Aqueous Formulation Stability −20° C.
(5 mg/mL (R,R)-pyrodach-2 in 10 mM Bicarbonate Buffer at pH 8.6) filled in 10 mL vials

| Parameter | Initial | 1 week | 2 week | 3 week | 1 month | 2 month | 3 month | 4 month | 6 month | 9 month | 12 month |
|---|---|---|---|---|---|---|---|---|---|---|---|
| Appearance | Clear solution with no visible particulates | NT | NT | NT | Pale yellow solution with no visible particulates | NT | NT | NT | Clear solution with yellow precipitation upon equilibration[1] | NT | Clear solution with yellow-brown precipitation upon equilibration[2] |
| Potency (Assay) | 100.3% | NT | NT | NT | 97.5% | NT | NT | NT | 98.4% | NT | 86.1% |
| Purity (% Area) | 98.04% | NT | NT | NT | 97.08% | NT | NT | NT | 96.36% | NT | 90.94% |
| Unknown Impurities | | | | | | | | | | | |
| RRT~0.29 | 0.11% | NT | NT | NT | 0.16% | NT | NT | NT | 0.23% | NT | 0.13% |
| RRT~0.41 | ND | NT | NT | NT | 0.07% | NT | NT | NT | 0.45% | NT | 5.26% |
| RRT~0.44 | ND | NT | NT | NT | 0.09% | NT | NT | NT | ND | NT | ND |
| RRT~0.49 | 0.62% | NT | NT | NT | 0.94% | NT | NT | NT | 1.41% | NT | 1.19% |
| RRT~0.59 | ND | NT | NT | NT | 0.09% | NT | NT | NT | 0.15% | NT | 0.27% |
| RRT~0.62 | ND | NT | NT | NT | 0.12% | NT | NT | NT | ND | NT | 0.43% |
| RRT~0.73 | 1.05% | NT | NT | NT | 1.12% | NT | NT | NT | 0.84% | NT | 0.88% |
| RRT~1.69 | ND | NT | NT | NT | ND | NT | NT | NT | 0.22% | NT | 0.25% |
| RRT~2.96 | ND | NT | NT | NT | ND | NT | NT | NT | ND | NT | 0.08% |
| RRT~3.02 | ND | NT | NT | NT | ND | NT | NT | NT | ND | NT | 0.09% |
| RRT~3.12 | ND | NT | NT | NT | 0.05% | NT | NT | NT | 0.08% | NT | 0.05% |
| RRT~3.24 | ND | NT | NT | NT | ND | NT | NT | NT | ND | NT | 0.06% |
| RRT~3.30 | ND | NT | NT | NT | 0.05% | NT | NT | NT | 0.06% | NT | 0.13% |
| RRT~3.33 | ND | NT | NT | NT | 0.06% | NT | NT | NT | 0.05% | NT | 0.06% |
| RRT~3.70 | ND | NT | NT | NT | ND | NT | NT | NT | ND | NT | 0.09% |
| RRT~4.02 | ND | NT | NT | NT | 0.08% | NT | NT | NT | 0.09% | NT | 0.14% |
| pH | 8.60 | NT | NT | NT | 8.77 | NT | NT | NT | 8.72 | NT | 8.83 |

ND = Not Detected, or <0.05%;
NT = Not Tested;
RRT = Relative Retention time
[1]Appeared to resolubilize with manual agitation and brief sonication
[2]Not able to resolubilize with manual agitation and brief sonication Comparison of stability data for a 5 mg/mL concentration (R,R)-pyrodach-2 solution in 10 mM potassium phosphate buffer adjusted to pH 7.0-7.5 at 25° C./60% RH in Table 4 with that of a same concentration formulation containing ~0.5 molar equivalent of added pyrophosphate in Table 11, shows the addition of pyrophosphate ion dramatically retards the rate of (R,R)-pyrodach-2 degradation such that the stability of the formulation with pyrophosphate at 25° C. is comparable/superior to that of the formulation without the added pyrophosphate stored at refrigerated conditions. Stability data on the formulation with added pyrophosphate at 40° C./75% RH in Table 12 is even more dramatic. Kinetic/design of experiment studies were utilized to demonstrate the effect of pyrophosphate on buffered aqueous ready-to-use formulations of (R,R)-pyrodach-2 (Example 9).

The data further demonstrate that addition of a buffering salt such as phosphate or carbonate/bicarbonate is unnecessary to achieve pH control but rather the buffering capacity of pyrophosphate in the physiological pH range is sufficient to control pH in an aqueous formulation of (R,R)-pyrodach-2. From a clinical perspective, maintaining the amount of pyrophosphate ion at a minimum in an aqueous formulation of (R,R)-pyrodach-2 is desirable. A ratio of 1 molar equivalent of pyrophosphate ion to (R,R)-pyrodach-2 was found to provide sufficient stability to aqueous (R,R)-pyrodach-2 solutions at physiological pH such that a formulated ready-to-use formulation would have a commercial shelf-life of several years on storage at standard long-term International Committee on Harmonization (ICH) storage conditions of 25° C./60% RH (i.e. ambient temperature). More optimally a molar ratio of ~0.5 mole of pyrophosphate ion to (R,R)-pyrodach-2 was found to provide acceptable stability for an aqueous ready-to-use formulation of (R,R)-pyrodach-2. Most preferably the formulation consists of a 5 mg/mL aqueous solution of (R,R)-pyrodach-2 in pyrophosphate adjusted to pH 7-7.5. Further, the inclusions of pyrophosphate ion in the formulation, or as the exclusive buffering agent, eliminates the potential for precipitation of impurities and in particular the highly insoluble (R,R)-pyrodach-2 dimer impurity from an aqueous ready-to-use formulations of (R,R)-pyrodach-2.

TABLE 11

(R,R)-Pyrodach-2 Ready-to-use Aqueous Formulation Stability 25° C./60% RH
(5 mg/mL (R,R)-pyrodach-2 in 10 mM Sodium Phosphate Buffer, 5.2 mM Sodium
Pyrophosphate at pH 7.5) filled in 10 mL vials

| Parameter | Initial | 1 Month | 2 Months | 3 Months | 6 Months | 9 Months |
|---|---|---|---|---|---|---|
| Appearance | Clear Colorless Solution Free of Particulates | Clear Colorless Solution Free of Particulates | Clear Colorless Solution Free of Particulates | Clear Colorless Solution Free of Particulates | Clear Colorless Solution Free of Particulates | Clear Colorless Solution Free of Particulates |
| Potency (Assay) | 102.0% | 102.2% | 103.8% | 101.4% | 102.8% | 101.7% |
| Individual Related Substances | | | | | | |
| RRT 0.28-0.29 | 0.14% | 0.10% | 0.20% | 0.17% | 0.17% | 0.18% |
| RRT 0.50-0.51 | 0.08% | 0.08% | 0.15% | 0.11% | 0.12% | 0.21% |
| RRT 0.58 | 0.34% | 0.39% | 0.38% | 0.43% | 0.44% | 0.42% |
| RRT 0.73-0.74 | 0.83% | 0.71% | 0.92% | 0.88% | 0.81% | 0.27% |
| RRT 0.92 | 0.05% | ND | ND | ND | ND | ND |
| RRT 1.57 | 0.12% | ND | ND | ND | ND | ND |
| PT-112 Dimer | 0.16% | ND | ND | ND | ND | ND |
| Total Related Substances | 1.7% | 1.3% | 1.6% | 1.6% | 1.5% | 1.20% |
| pH | 7.5 | 7.6 | 7.6 | 7.6 | 7.6 | 7.6 |

TABLE 12

(R,R)-Pyrodach-2 Ready-to-use Aqueous Formulation Stability 40°
C./75% RH (5 mg/mL (R,R)-pyrodach-2 in 10 mM Sodium Phosphate Buffer,
5.2 mM Sodium Pyrophosphate at pH 7.5) filled in 10 mL vials

| Parameter | Initial | 1 Month | 2 Months | 3 Months | 6 Months |
|---|---|---|---|---|---|
| Appearance | Clear Colorless Solution Free of Particulates | Clear Colorless Solution Free of Particulates | Clear Colorless Solution Free of Particulates | Clear Colorless Solution Free of Particulates | Clear Colorless Solution Free of Particulates |
| Potency (Assay) | 102.0% | 101.6% | 103.8% | 101.5% | 102.8% |
| Individual Related Substances | | | | | |
| RRT 0.28-0.29 | 0.14% | 0.10% | 0.19% | 0.16% | 0.17% |
| RRT 0.50-0.51 | 0.08% | 0.10% | 0.19% | 0.16% | 0.22% |
| RRT 0.58 | 0.34% | 0.41% | 0.41% | 0.48% | 0.47% |
| RRT 0.73-0.74 | 0.83% | 0.68% | 0.88% | 0.86% | 0.81% |
| RRT 0.92 | 0.05% | ND | ND | ND | ND |
| RRT 1.57 | 0.12% | ND | ND | ND | ND |
| RRT 3.66-3.71 | ND | ND | 0.07% | 0.11% | 0.18% |
| PT-112 Dimer | 0.16% | ND | ND | ND | ND |
| Total Related Substances | 1.7% | 1.3% | 1.7% | 1.8% | 1.9% |
| pH | 7.5 | 7.6 | 7.6 | 7.5 | 7.5 |

Evidence that added pyrophosphate reverses the formation of PT-112 dimer in aqueous formulations of PT-112 was shown in the following experiment. A 5 mg/mL aqueous solution of PT-112 was prepared by dissolving PT-112 in 10 mM potassium phosphate buffer containing added potassium hydroxide such that the final solution pH was ~6.5. The solution was allowed to stir at ambient temperature for about 24 hours during which time the PT-112 dimer level increased from about 0.33% in the API to about 1.02% in the formulated solution. On subsequent pH adjustment of a portion of the solution to ~pH 7.5 with potassium hydroxide, the concentration of dimer was observed to progressively decrease over a 7 day period at ambient temperature accompanied by a corresponding increase in the RRT 3.1-3.2 impurity. However on pH of a portion of the solution with potassium hydroxide to ~pH 7.5 and the addition of 0.5 eq. of pyrophosphate, the level of dimer was observed to progressively decrease to effectively non-detectable level after 9 days at ambient temperature. The decrease was not accompanied by the formation of the RRT 3.1-3.2 impurity; nor the formation of any new impurities, rather an increase in the concentration of PT-112 was observed.

Example 1

Impact of Buffer Strength

Buffer Solution Preparation
   10 mM Sodium Phosphate, pH 7
   200 mL of 10 mM sodium phosphate, dibasic adjusted with 177 mL of 10 mM sodium phosphate, monobasic
   Final pH 7.02
   100 mM Sodium Phosphate, pH 7
   200 mL of 100 mM sodium phosphate, dibasic and adjusted with 138 mL of 100 mM sodium phosphate, monobasic Final pH 6.98
10 mM Potassium Phosphate, pH 7
200 mL of 10 mM potassium phosphate, dibasic adjusted with ~126 mL of 10 mM potassium phosphate, monobasic
Final pH 7.01
100 mM Potassium Phosphate, pH 7
200 mL of 100 mM potassium phosphate, dibasic adjusted with ~125 mL of 10 mM potassium phosphate, monobasic
Final pH 7.02
10 mM Sodium Carbonate
No pH adjustment performed
Final pH 10.84
100 mM Sodium Carbonate
No pH adjustment performed
Final pH 11.39
10 mM Sodium Bicarbonate
No pH adjustment performed
Final pH 8.18
100 mM Sodium Bicarbonate
No pH adjustment performed
Final pH 8.06

Figure 2:
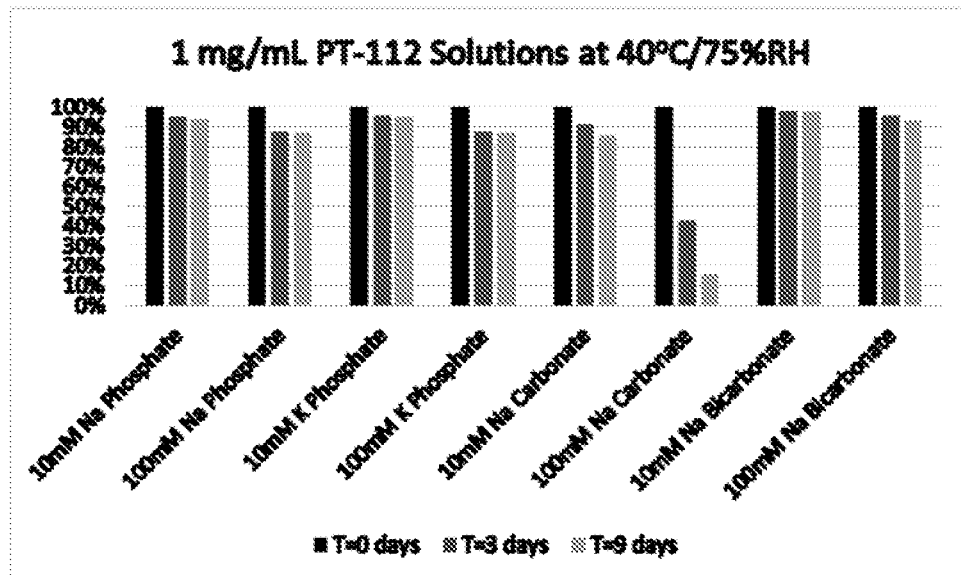
FIG. 2 illustrates the potency of capped 1 mg/mL (R,R)-pyrodach-2 solutions in various buffers stored in stability chambers controlled at 40° C./75% RH, as monitored by HPLC.

(R,R)-Pyrodach-2 was dissolved in each of these buffers to prepare at 1 mg/mL solution. The potency of capped solutions stored in stability chambers controlled at 25° C./60% RH and 40° C./75% RH was monitored by HPLC. See FIG. 1 and FIG. 2.

Example 2

Impact of pH on Phosphate Buffer Solution Stability

Buffer Solution Preparation
10 mM Potassium Phosphate, pH 6.5
50 mL of 10 mM potassium phosphate, dibasic adjusted with ~145 mL of 10 mM potassium phosphate, monobasic
Final pH 6.50
10 mM Potassium Phosphate, pH 7
200 mL of 10 mM potassium phosphate, dibasic adjusted with ~126 mL of 10 mM potassium phosphate, monobasic
Final pH 7.01
10 mM Potassium Phosphate, pH 7.5
50 mL of 10 mM potassium phosphate, dibasic adjusted with ~14 mL of 10 mM potassium phosphate, monobasic
Final pH 7.50
10 mM Potassium Phosphate, pH 8.0
50 mL of 10 mM potassium phosphate, dibasic adjusted with ~4 mL of 10 mM potassium phosphate, monobasic
Final pH 8.00
10 mM Potassium Phosphate, pH 8.5
50 mL of 10 mM potassium phosphate, dibasic adjusted with ~1 mL of 10 mM potassium phosphate, monobasic
Final pH 8.49
10 mM Potassium Phosphate, pH 9.0
90 mL of 10 mM potassium phosphate, dibasic adjusted with <1 mL of 10 mM potassium phosphate, monobasic
Final pH 9.02

Figure 3:
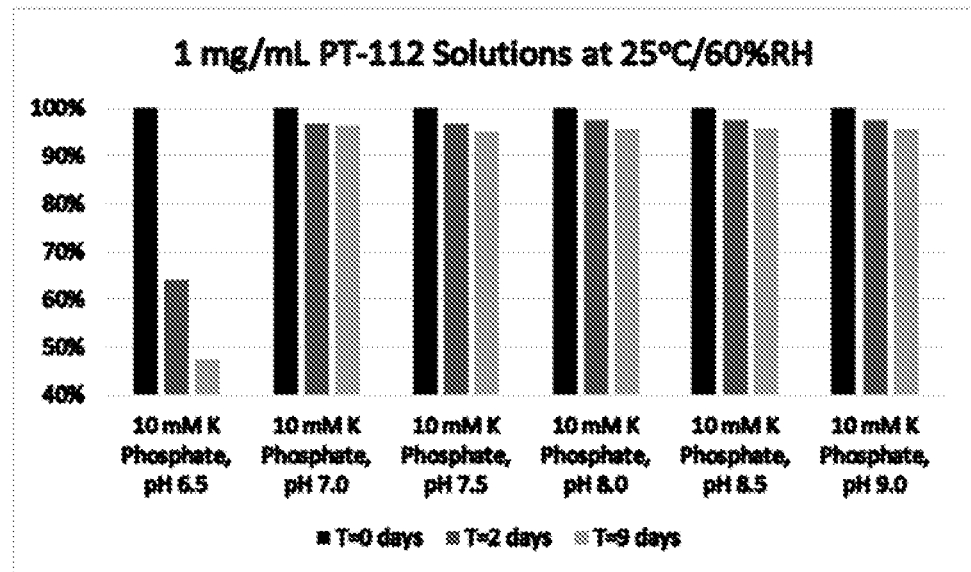
FIG. 3 illustrates the potency of capped 1 mg/mL (R,R)-pyrodach-2 solutions in a 10 mM potassium phosphate buffer at various pH's stored in stability chambers controlled at 25° C./60% RH as monitored by HPLC.
Figure 4:
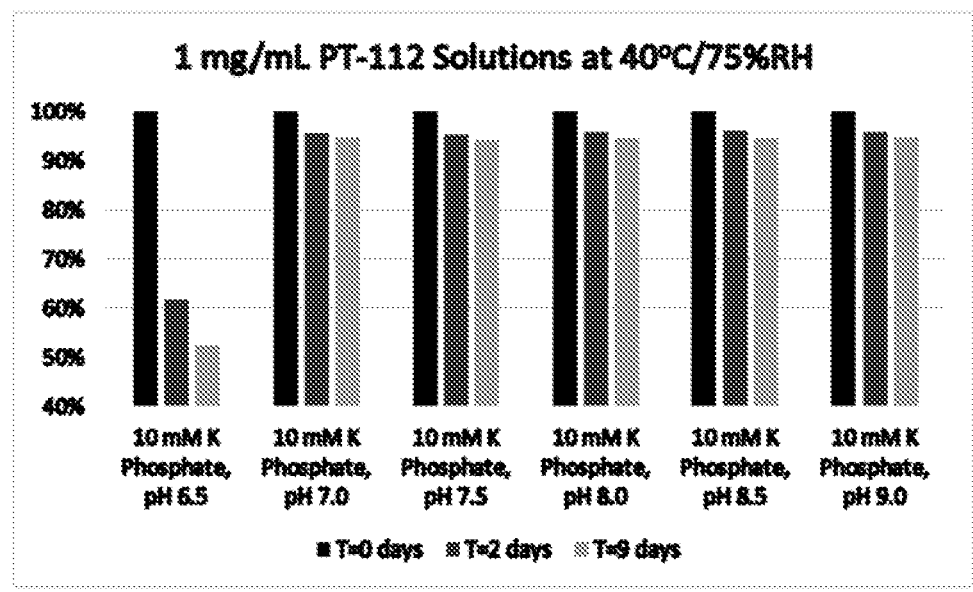
FIG. 4 illustrates the potency of capped 1 mg/mL (R,R)-pyrodach-2 solutions in a 10 mM potassium phosphate buffer at various pH's stored in stability chambers controlled at 40° C./75% RH as monitored by HPLC.

(R,R)-pyrodach-2 was dissolved in each of these buffers to prepare at 1 mg/mL solution. The potency of capped solutions stored in stability chambers controlled at 25° C./60% RH and 40° C./75% RH was monitored by HPLC, from which the data reported at T=3 days for pH 7.0 buffered solution are shown in FIG. 3 and FIG. 4, respectively.

Example 3

HPLC System

| Parameter | Condition |
|---|---|
| Column | Waters XSelect HSS T3, 4.6 mm × 100 mm, 3.5 μm |
| Stroke Volume | 100 μL |
| Column Temperature | 10.0° C. ± 2.0° C. |
| Sample Temperature | Ambient |
| Mobile Phase A | 50 mM Sodium Phosphate, pH 2.0 |
| Mobile Phase B | 100% Acetonitrile |
| Diluent | 20 mM Sodium Pyrophosphate |
| Injection Volume | 6 μL |
| Run Time | 24 minutes |
| Detection Wavelength | 205 nm |

| Time (Minutes) | Flow Rate (mL/min) | % Mobile Phase A | % Mobile Phase B |
|---|---|---|---|
| 0.00 | 1.5 | 100.0 | 0.0 |
| 4.93 | 1.5 | 100.0 | 0.0 |
| 14.53 | 1.5 | 90.0 | 10.0 |
| 16.53 | 1.5 | 100.0 | 0.0 |
| 24.00 | 1.5 | 100.0 | 0.0 |

Example 4

(R,R)-Pyrodach-2 Ready-to-Use Formulation 5 mg/mL in 10 mM Sodium Bicarbonate pH 9.0-9.5 (Pharmatek (R,R)-Pyrodach-2 Prototype Stability Protocol)

Transfer 1680.0 mg±0.5 mg of sodium bicarbonate to a 2-L volumetric flask.
Fill flask to approximately 75% volume with water, swirl as needed to dissolve all solids.
Volumetrically transfer 32.0 mL of 1N NaOH to flask.
Dilute to volume with water and mix well.
Record pH of final solution. This is the diluent.
Transfer 7653.1 mg±0.5 mg of (R,R)-pyrodach-2 to a compounding vessel.
Transfer 1500 mM of the diluent to the vessel and stir to dissolve solids.
Record pH of final solution.
Pass entire solution through a 0.22 μm sterile filter membrane into a sterile collection vessel.
Calculate (R,R)-pyrodach-2 solution concentration $$[(R, R)\text{-}pyrodach\text{-}2], \text{mg/mL} = \frac{\text{Wt of } (R, R)\text{-}pyrodach\text{-}2, \text{mg} * (R, R)\text{-}pyrodach\text{-}2 \text{ purity}}{1500 \text{ mL}}$$

Conduct the following in a laminar flow hood; fill 10-mL sterile Type 1 borosilicate glass vials with a fill volume of 10-mL, stopper the vials with 20 mm sterile rubber stoppers and crimp-sealed with 20 mm crimp tops.

Place vials in 25° C./60% RH, 2-8° C. and −20° C. stability chambers. HPLC method in Example 3 to monitor purity and impurities.

Example 5

(R,R)-Pyrodach-2 15 mg/mL Ready-to-Use Formulation

V is the required final volume of solution to be made
Dissolve V×11.4 mg sodium phosphate, tribasic (dodecahydrate)+V×4.26 mg sodium, dibasic (anhydrous) in V mL of distilled water. Stir until buffer salts are dissolved.
To the stirred buffer solution add V×15 mg quantity of (R,R)-pyrodach-2; stir on a magnetic stirrer until the solid (R,R)-pyrodach-2 dissolves completely (10-30 minutes)
Record the solution pH.
Adjust the pH, if needed, to 7.0-7.4 by the adding V×1.8 mg of sodium phosphate, tribasic (dodecahydrate) with stirring to dissolve, record the final pH.
To make a (R,R)-pyrodach-2 solution of a lower concentration, dilute the above 15 mg/mL (R,R)-pyrodach-2 solution with an appropriate amount of vehicle.

Example 6

(R,R)-Pyrodach-2 Ready-to-Use Formulation 5 mg/mL in 10 mM Potassium Phosphate pH 7.2-7.5

Transfer 4564.6 mg±0.5 mg of potassium phosphate dibasic, trihydrate to a 2-L volumetric flask.
Fill flask to approximately 75% volume with water, swirl as needed to dissolve all solids.
Volumetrically transfer 32.0 mL of 1N KOH to flask.
Dilute flask to volume with water and mix well.
Record pH of final solution. This is the diluent.
Transfer 7653.1 mg±0.5 mg of (R,R)-pyrodach-2 to a compounding vessel.
Transfer 1500 mL of the diluent to the vessel and stir to dissolve solids.
Record pH of final solution.
Pass entire solution through a 0.22 μm sterile filter membrane into a sterile collection vessel.
Calculate (R,R)-pyrodach-2 solution concentration $$[(R,R)\text{-}pyrodach\text{-}2], \text{mg/mL} = \frac{\text{Wt of } (R,R)\text{-}pyrodach\text{-}2, \text{mg} * (R,R)\text{-}pyrodach\text{-}2 \text{ purity}}{1500 \text{ mL}}$$

Example 7

(R,R)-Pyrodach-2 Ready-to-Use Formulation 5 mg/mL in 10 mM Sodium Phosphate, 5.2 mM Sodium Pyrophosphate pH 7.5

Transfer 1419.6 mg±14.0 mg of dibasic sodium phosphate anhydrous to a 1-L volumetric flask.
Transfer 2298.5 mg±23.0 mg of tetrasodium pyrophosphate decahydrate into the same 1-L volumetric flask.
Fill flask to approximately 75% volume with sterile water for injection, swirl as needed to dissolve all solids.
Volumetrically transfer 8.0 mL of 1N NaOH to flask.
Dilute flask to volume with water and mix well.
Record the pH of final solution. This is the vehicle.
Determine the tare weight of a 500-mL compounding vessel with stir bar.
Transfer 2500.1 mg±25.0 mg of (R,R)-pyrodach-2 to the vessel.
Transfer 450.0 g±0.1 g of the vehicle to the vessel and stir to dissolve solids.
Determine the initial pH of the solution.
Slowly adjust the pH of the solution to 7.5±0.1 by adding additional N NaOH.
Determine the gross solution weight and dilute the solution weight to 500.0 g±0.1 g by adding additional vehicle into the compounding vessel. Density=1.00 g/mL.
Stir the final solution for an additional 5 minutes.
Determine the pH of final solution.
Pass the entire solution through a 0.22 μm PVDF Stericup filter into a sterile collection vessel.
Conduct the following in a laminar flow hood; fill 10-mL sterile tubing vials with 10 mL of solution, stoppered with a sterile Flurotec stopper, and crimp-capped with a flip-off seal.
Place vials in 40° C./75% RH and 25° C./60% RH stability chambers. HPLC method in Example 3 to monitor purity and impurities.

Example 8

(R,R)-Pyrodach-2 Ready-to-Use Formulation 5 mg/mL in 5.2 mM Sodium Pyrophosphate pH 7.5

Transfer 2298.5 mg±23.0 mg of tetrasodium pyrophosphate decahydrate into a 1-L volumetric flask.
Fill flask to approximately 75% volume with sterile water for injection, swirl as needed to dissolve all solids.
Volumetrically transfer 14.5 mL of 1N NaOH to flask.
Dilute flask to volume with water and mix well.
Record the pH of final solution. This is the vehicle.
Determine the tare weight of a 500-mL compounding vessel with stir bar.
Transfer 2500.1 mg±25.0 mg of (R,R)-pyrodach-2 to the vessel.
Transfer 450.0 g±0.1 g of the vehicle to the vessel and stir to dissolve solids.
Determine the initial pH of the solution.
Slowly adjust the pH of the solution to 7.5±0.1 by adding additional 0.1N NaOH.
Determine the gross solution weight and dilute the solution weight to 500.0 g±0.1 g by adding additional vehicle into the compounding vessel. Density=1.00 g/mL.
Stir the final solution for an additional 5 minutes.
Determine the pH of final solution.
Pass the entire solution through a 0.22 μm PVDF Stericup filter into a sterile collection vessel.
Conduct the following in a laminar flow hood; fill 10-mL sterile tubing vials with 10 mL of solution, stoppered with a sterile Flurotec stopper, and crimp-capped with a flip-off seal.
Place vials in 40° C./75% RH and 25° C./60% RH stability chambers. HPLC method in Example 3 to monitor purity and impurities.

Example 9

Design of Experiment Study on Pyrophosphate Ion Stabilization

The formulations used for the Design of Experiment study are listed in Table 11. The stability evaluation under the highly stressing temperature of 60° C. demonstrate that the addition of very small amounts of pyrophosphate ion, including as little as ~0.25 molar equivalent relative to the (R,R)-pyrodach-2 present, provides a dramatic decrease in the overall rate of (R,R)-pyrodach-2 degradation and in impurity appearance. Notably the data show that pyrophosphate ion results in the progressive disappearance of several impurities initially present in the aqueous solution resulting from impurities in the (R,R)-pyrodach-2 or which have formed during solution preparation. Specifically the presence of pyrophosphate results in the rapid disappearance of the (R,R)-pyrodach-2 dimer impurity and the RRT-3.1-3.2 impurity.

TABLE 11

(R,R)-Pyrodach-2 Pyrophosphate Design of Experiments Formulations

| Formulation No. | Phosphate concentration | Pyrophosphate concentration | pH |
|---|---|---|---|
| 1 | 10 mM | 10.305 mM | 6.5 |
| 2 | 10 mM | 10.305 mM | 7.5 |
| 3 | none | 10.305 mM | 7.5 |
| 4 | none | 10.305 mM | 6.5 |
| 5 | 10 mM | 5.153 mM | 6.5 |
| 6 | 10 mM | 5.153 mM | 7.5 |
| 7 | none | 5.153 mM | 7.5 |
| 8 | none | 5.153 mM | 6.5 |
| 9 | 10 mM | none | 6.5 |
| 10 | 10 mM | none | 7.5 |
| 11 | 10 mM | 1.0305 mM | 6.5 |
| 12 | 10 mM | 1.0305 mM | 7.5 |
| 13 | 10 mM | 2.577 mM | 7.5 |
| 14 | none | 5.135 mM | 8.5 |

Example 10

(R,R)-Pyrodach-2 Ready-to-Use Aqueous Formulation (5 mg/mL (R,R)-Pyrodach-2 in 10 mM Phosphate Buffer at pH 7) Filled in 10 mL Vials To a 36 ml glass beaker equipped with mechanical mixer was add 24645.5 g of sterile water for injection. With agitation 47.03 gm of dibasic potassium phosphate USP was added and the solids allowed to dissolve. To the stirred solution was added 253.8 gm of 1.00 N potassium hydroxide. Sterile water for injection USP (900.0 gm) was used as a rinse to facilitate both additions. With vigorous agitation, (R,R)-pyrodach-2 (201.87 gm) was slowly added and agitation continued until all of the solids dissolved. Sterile water for injection USP (900.0 gm) was used as a rinse to facilitate the addition. The pH was determined to be 6.7. A total of 85 mL of 1.00 N potassium hydroxide was added in 5.0 mL aliquots to adjust the pH to 7.3. The solution was sterile filtered through 0.22μ Millipore Millipack filter and aseptically filled, 10 ml top a vial in 10 mL in 10 cc Wheaton clear molded vails, stoppered with a 20 mm stopper and crimp seal capped.

The foregoing examples and description of certain preferred embodiments should be taken as illustrating, rather than as limiting, the present invention. As would be readily appreciated by a person skilled in the art, numerous variations and combinations of the features set forth above may be utilized without departing from the present invention.

What is claimed is:

1. A liquid pharmaceutical composition comprising a phosphaplatin compound of formula (I) or (II), or a pharmaceutically acceptable salt thereof, and an aqueous buffer solution having pH at about or above 7:

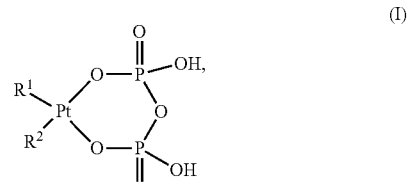

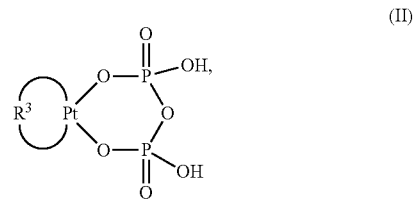

wherein $R^1$ and $R_2$ are each independently selected from the group consisting of substituted or unsubstituted aliphatic amines and substituted or unsubstituted aromatic amines; $R^3$ is selected from the group consisting of substituted or unsubstituted aliphatic 1,2-diamines and substituted or unsubstituted aromatic 1,2-diamines; and wherein the buffer solution comprises a pyrophosphate salt to stabilize the phosphaplatin compound, and the liquid pharmaceutical composition is a ready-to-use liquid formulation suitable for parenteral administration.

2. The liquid pharmaceutical composition of claim 1, wherein concentration of the phosphaplatin compound is about 20 mg/mL or less.

3. The liquid pharmaceutical composition of claim 2, wherein the concentration of the phosphaplatin compound is about 5 mg/mL.

4. The liquid pharmaceutical composition of claim 1, wherein the buffer comprises a sodium or potassium salt of phosphate or bicarbonate/carbonate.

5. The liquid pharmaceutical composition of claim 4, wherein the buffer salt concentration is between about 1 mM and about 100 mM.

6. The liquid pharmaceutical composition of claim 1, wherein the pH is in the range of about 7.0 to about 9.0.

7. The liquid pharmaceutical composition of claim 6, wherein the buffer is potassium phosphate; the concentration of the phosphaplatin compound is about 5 mg/mL and the pH is between about 7.0 and about 8.0.

8. The liquid pharmaceutical composition of claim 7, wherein the buffer concentration is about 10 mM.

9. The liquid pharmaceutical composition of claim 1, wherein the pyrophosphate salt is sodium pyrophosphate.

10. The liquid pharmaceutical composition of claim 9, wherein the molar ratio of pyrophosphate anion to the phosphaplatin compound is at least about 0.1 to about 1.

11. The liquid pharmaceutical composition of claim 9, wherein the concentration of the phosphaplatin compound is about 5 mg/mL, the pyrophosphate concentration is about 5.2 mM, and the pH is in the range of about 7.0 to about 8.0.

12. The liquid pharmaceutical composition of claim 1, wherein the phosphaplatin compound is a trans-1,2-cyclohexanediamine-(dihydrogen pyrophosphato)platinum(II) ("trans-pyrodach-2") complex.

13. The liquid pharmaceutical composition of claim 1, wherein the phosphaplatin compound is (R,R)-trans-1,2-cyclohexanediamine-(dihydrogen pyrophosphato)platinum (II) ("(R,R)-trans-pyrodach-2").

14. The liquid pharmaceutical composition of claim 1, wherein the phosphaplatin compound is (S,S)-trans-1,2-cyclohexanediamine-(dihydrogen pyrophosphato)platinum (II) ("(S,S)-trans-pyrodach-2").

15. The liquid pharmaceutical composition of claim 1, wherein the phosphaplatin compound is cis-1,2-cyclohexanediamine-(dihydrogen pyrophosphato)-platinum(II) ("cis-pyrodach-2").

16. A method of treating a cancer selected from the group consisting of gynecological cancers, genitourinary cancers, lung cancers, head-and-neck cancers, skin cancers, gastrointestinal cancers, breast cancers, bone and chondroital cancers, and hematological cancers the method comprising administering to a subject in need thereof a therapeutically effectively amount of the liquid pharmaceutical composition of claim 1.

17. A process of preparing a liquid pharmaceutical composition of phosphaplatin compound according to claim 1, the process comprising: a) dissolving a phosphaplatin compound in an aqueous buffer to obtain a solution comprising a sufficient amount of hydroxide base such that the pH remains at or above 7; b) adding a pyrophosphate salt to the solution to stabilize the phosphaplatin compound; c) optionally adding a hydroxide base to adjust the pH to a desired range; and d) filtering the solution to obtain a liquid formulation under sterile conditions, wherein the aqueous buffer is a phosphate buffer, a carbonate/bicarbonate buffer, or a combination thereof.

18. The process of claim 17, wherein the pH of the liquid formulation is in the range of about 7.0 to about 9.0.

19. The process of claim 17, wherein the pyrophosphate salt is sodium pyrophosphate.

20. The process of claim 17, further comprising d) filling the solution into a vial, stoppering and capping the vial in a sterile environment so that the formulation is ready for use.

* * * * *